(12) United States Patent
Sarrazin et al.

(10) Patent No.: US 6,208,890 B1
(45) Date of Patent: Mar. 27, 2001

(54) DEVICE AND METHOD FOR MEASURING THE COMPOSITION OF THE BODY

(75) Inventors: Michel Sarrazin, Massingy; Alain Duborper, Sales, both of (FR)

(73) Assignee: SEB, S.A. (FR)

(*) Notice: Subject to any disclaimer, the term of this patent is extended or adjusted under 35 U.S.C. 154(b) by 0 days.

(21) Appl. No.: 09/260,154

(22) Filed: Mar. 1, 1999

(30) Foreign Application Priority Data

Mar. 3, 1998 (FR) .................................................. 98 02550

(51) Int. Cl.[7] .......................................................... A61B 5/05
(52) U.S. Cl. .............................................................. 600/547
(58) Field of Search ................................................ 600/547

(56) References Cited

U.S. PATENT DOCUMENTS 4,911,175 * 3/1990 Shizgal ................................. 600/547
5,579,782 * 12/1996 Masuo ................................. 600/547
6,016,445 * 1/2000 Baura ................................... 600/547

FOREIGN PATENT DOCUMENTS

| 9005415 | 12/1990 | (DE) . |
| 2698779 | 6/1994 | (FR) . |
| 8303746 | 11/1983 | (WO) . |
| 9608198 | 3/1996 | (WO) . |
| 9700642 | 1/1997 | (WO) . |

* cited by examiner

Primary Examiner—William E. Kamm
(74) Attorney, Agent, or Firm—Harness, Dickey & Pierce, P.L.C.

(57) ABSTRACT

A device for measuring the composition of the body of a person includes a first electronic module which measures a bioelectrical impedance and including at least one current source which delivers a variable electrical signal that passes through the body of the person when the person is connected to the measuring device. The electrical signal is a square-wave the duration of which is variable to determine the global impedance, the intracellular impedance and the extracellular impedance of the body of the person directly.

9 Claims, 4 Drawing Sheets

DEVICE AND METHOD FOR MEASURING THE COMPOSITION OF THE BODY

BACKGROUND OF THE INVENTION

1. Field of the Invention

The present invention concerns a device and a method for measuring the composition of the body of a person, said device including a first electronic module which measures the bioelectric impedance of the body and including a current source which delivers a variable electrical signal that passes through the body of the person when the latter is connected to the measuring device.

2. Description of the Prior Art

The composition of the body is measured to assess the nutritional requirement of a person and, as is known per se, by measuring the bioelectric impedance of the body of the person. This provides information on the ratio of lean to fat body mass and the amount of water in the body.

Prior art methods and devices for measuring bioelectric impedance are based on the principle of applying a low alternating current (50 $\mu$A to 1500 $\mu$A) to the body of the person using two or four electrodes, as shown diagrammatically in FIG. 1. The potential difference that appears between the electrodes is used to calculate the overall impedance Z of the body, which is regarded as a suspension of cells in an electrolytic solution. The global impedance Z of the body is determined from an electrical model of the body, such as the Fricke model shown in FIG. 2, allowing for the frequency $f_C$ of the current used and the resistance to the flow of electrical current due to water and to intracellular and extracellular electrolytes. The respective resistances of said electrolytes are represented by $R_I$ and by $R_E$ in the Fricke model. The calculated bioelectrical impedance also allows for the reactance $X_{fc}$ of the body membrane, the effect of which is to induce a phase-shift $\Theta$ between the applied current and the measured voltage. Referring to FIG. 2, $R_1$, $R_2$, $C_1$ and $C_2$ respectively represent the contact resistances and capacitances of the electrodes. These factors are related by the following equations:

$$Z^2 = R^2 + X_{fc}^2$$

$$X_{fc} = |Z| \times \sin \Theta$$

$$R = |Z| \times \cos \Theta$$

The locus of impedance of the above equations is a semicircle centered on the abscissa axis (see FIG. 3).

A drawback of devices based on the above method is that a plurality of excitation frequencies must be used to determine the impedance of the body from the FIG. 3 diagram. Furthermore, it has been found that an excessively low frequency is unable to explore the intracellular sector correctly because the capacitance of the membrane represents too high a reactance at this frequency. Moreover, these devices make it necessary to measure the phase-shift $\Theta$, which is indispensable not only for measuring the impedance Z but also for estimating the resistive part R, which gives the most accurate calculation of lean body mass and total water.

Devices using four electrodes and a single frequency of 50 kHz for which the phase-shift is maximum are known per se. These devices cannot measure specifically the intracellular impedance $R_I$ and the extracellular impedance $R_E$ of the body. They can measure only the global impedance of the body.

The aim of the present invention is to overcome the above drawbacks.

SUMMARY OF THE INVENTION

The invention consists in a device for measuring the composition of the body of a person including a first electronic module adapted to measure a bioelectrical impedance and including at least one current source adapted to deliver a variable electrical signal that passes through the body of the person when the person is connected to the measuring device, wherein the electrical signal is a squarewave the duration of which is variable to determine the global impedance, the intracellular impedance and the extracellular impedance of the body of the person directly.

Varying the duration of the squarewave signal enables the equivalent resistance of the Fricke model to be measured without using a plurality of frequencies. Also, the capacitive effect of the cellular membranes can be determined directly from the measured intracellular and extracellular impedances.

To adapt the measurement to physiologically different persons, the frequency of the electrical signal is advantageously chosen in the range 2 kHz to 400 kHz.

Other features and advantages of the invention will emerge from the following description given by way of nonlimiting example and with reference to the accompanying drawings.

DETAILED DESCRIPTION OF THE PREFERRED EMBODIMENTS

Figure 4:
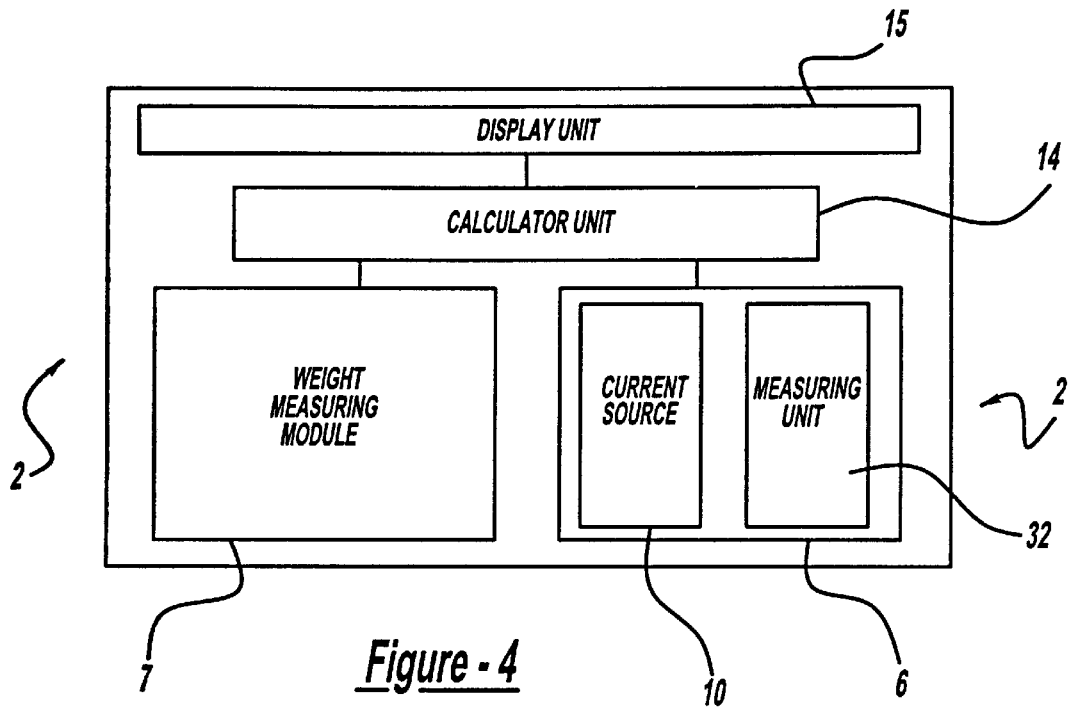
FIG. 4 represents a block diagram of a device in accordance with the invention for measuring fat body mass.

FIG. 4 is a diagram showing a device 2 for measuring the composition of the body of a person (or of an animal), said device including a first electronic module 6 for measuring the bioelectrical impedance of the body and including a current source 10 which delivers a variable electrical signal 11 which passes through the body of the person when the latter is connected to the device 2.

The device 2 also includes a second electronic module 7 for measuring the weight of the individual. The first module 6 and the second module 7 are connected to a calculator unit 14 which can be a microprocessor or a microcontroller adapted to carry out the necessary processing. Said calculator unit 14 receives the respective measured values of the weight and the bioelectrical impedance and calculates the fat body mass and the lean body mass of the person, on the basis of those values and employing formulae known per se and described in detail in French patent No. 2 698 779. The calculator unit 14 is also connected to display means 15 for displaying said measured values and said calculated values simultaneously or sequentially for real time monitoring of changes in the measured values.

Figure 5:
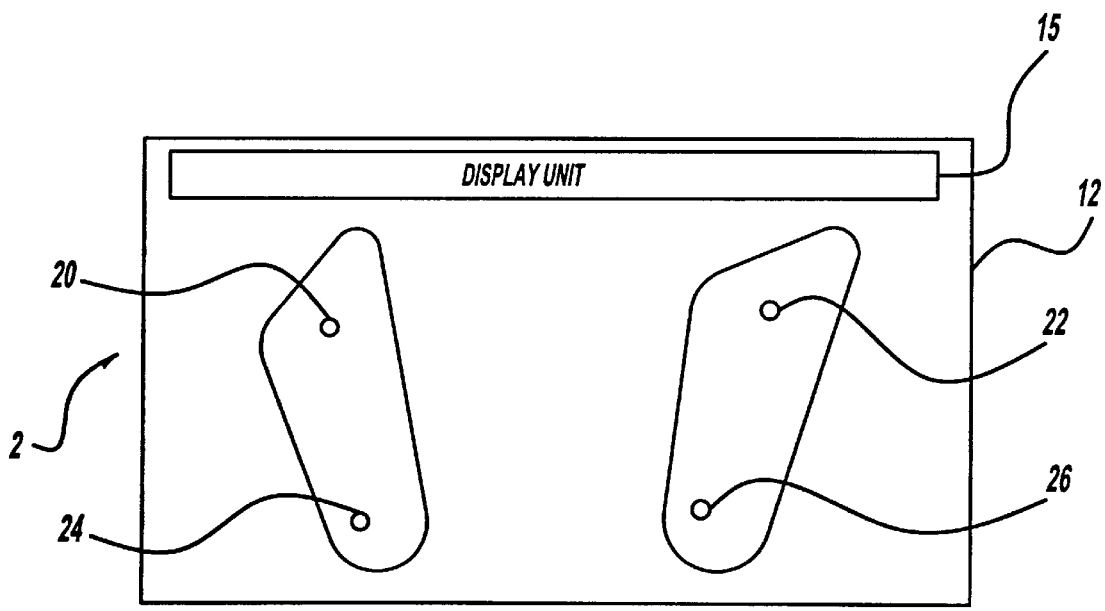
FIG. 5 is a diagrammatic plan view of the device from FIG. 4.

As shown in FIG. 5, the device 2 includes two excitation electrodes 20, 22 designed to apply the electrical signal 11 between first and second points on the body of the person and two measuring electrodes 24 and 26 between which an electrical voltage 30 is measured. The electrodes 24 and 26 are connected to a measuring unit 32 integrated into the second electronic module 7.

In a preferred embodiment of the invention the electrical signal 11 delivered by the current source 10 is a squarewave the duration of which can be adjusted by the processor unit 14 to suit the measurements and the processing to be carried out.

Figure 8:
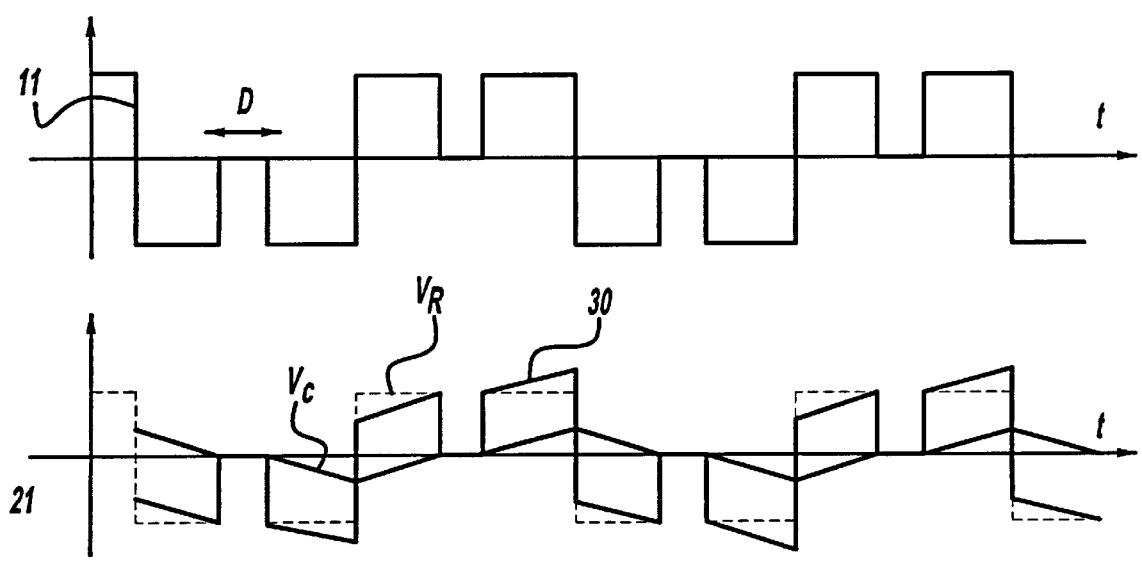
FIG. 8 is a diagram showing a variant of the current used in a device in accordance with the invention.

As shown in FIG. 8, the electrical signal 11 can be canceled for a predetermined period d to cancel totally the capacitive effect of the cellular membranes. Said electrical signal 11 can also be maintained at a constant value for a time period determined beforehand by the user. Said time period can be set by programming the calculator unit 14 or by external control means that the user can manipulate during measurement.

Figure 7:
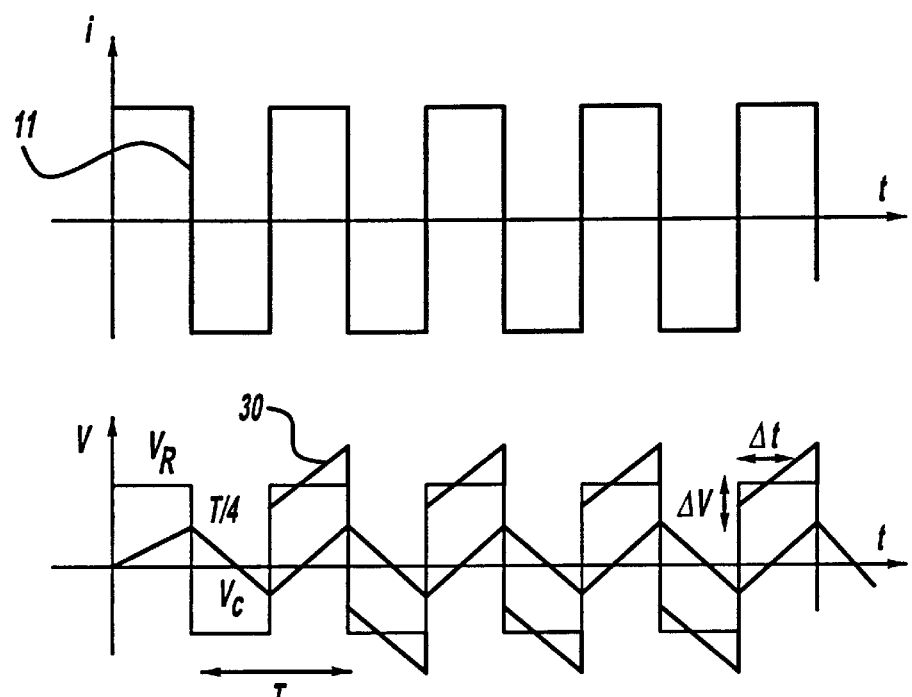
FIG. 7 is a diagram showing the waveform of an electrical current delivered by a source included in a device in accordance with the invention.

As shown in FIG. 7, the capacitive part of the dipole representing the body is charged with a time constant $R_I.C$ while the resistive part tracks perfectly the ramp of the signal 11. The charging line VC of the capacitor C periodically intersects the line of the resistive part. By carrying out the measurement at this precise time, it is possible to calculate the resistance R equivalent to the resistances $R_E$ and $R_I$ in parallel.

The resistance $R_E$ is determined from the equation:

$$R_E=(V_b-V_c)/i,$$

the voltages $V_b$ and $V_c$ being measured at a time corresponding to saturation of the capacitor C. The resistance RI is deduced from the equation $$R=(R_E \times R_I)/(R_E+R_I)$$

and the capacitance C is calculated from the equation $\Delta V=\Delta t.i/C$ in which $\Delta V$ represents a variation of the voltage $V_c$ during a time period $\Delta t$.

The measuring method therefore consists in applying the squarewave signal 11 between the excitation electrodes 20 and 22 and measuring the voltage 30 between the measuring electrodes 24 and 26 at times at which the tissue of the body of the person has a minimum effect or even no effect. To this end, the measuring unit 32 is programmed to capture the measured values of the voltage 30 each time the voltage $V_c$ passes through zero. This measurement is effected relative to a stable reference voltage obtained across a precision resistor $R_r$.

Figure 1:
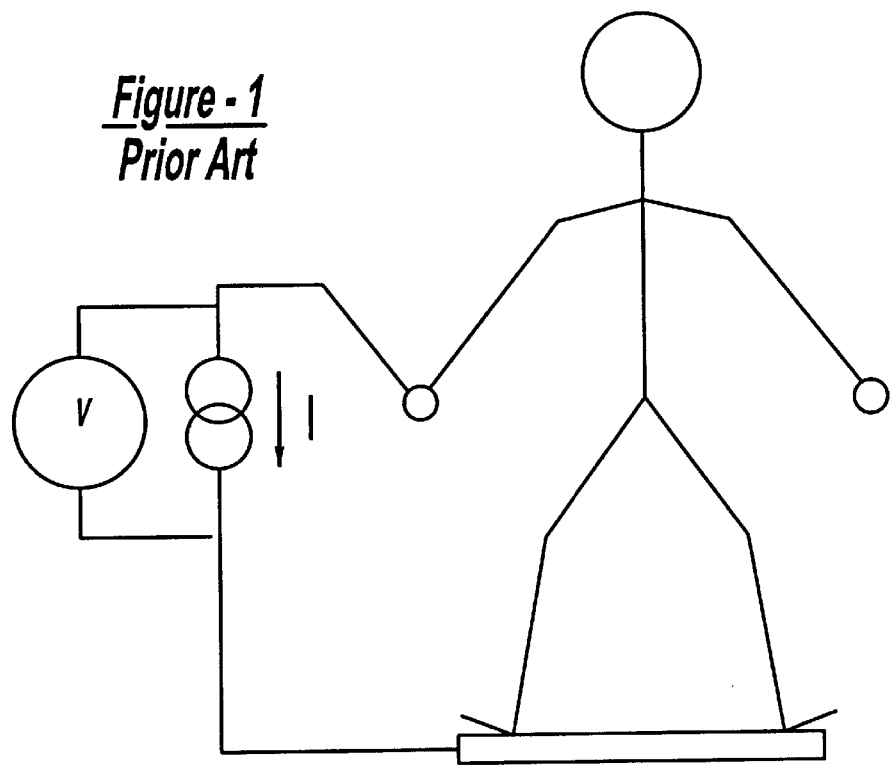
FIG. 1 is a diagram showing the prior art principle of measuring bioelectrical impedance based on the use of two electrodes.
Figure 2:
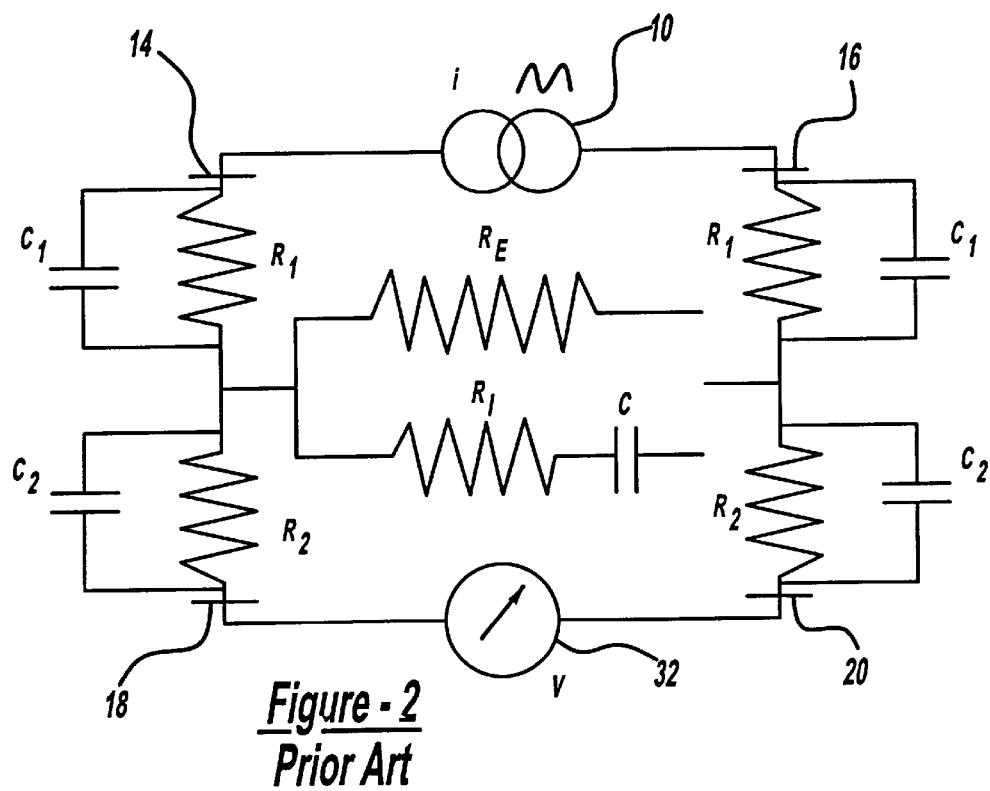
FIG. 2 is a diagrammatic representation of a prior art measuring device with four electrodes.
Figure 3:
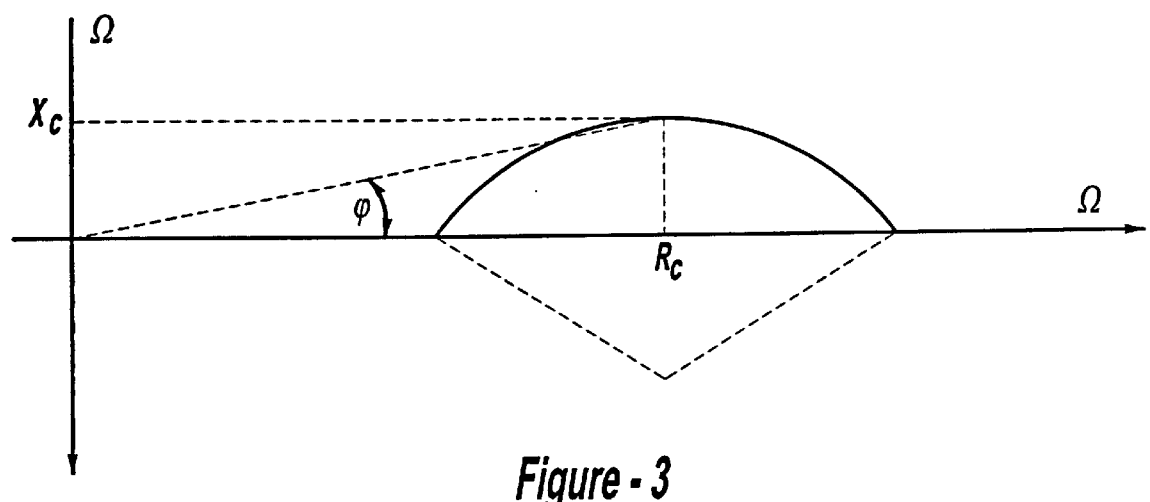
FIG. 3 shows an impedance diagram used in the prior art methods to calculate the bioelectric impedance of the human body.
Figure 6:
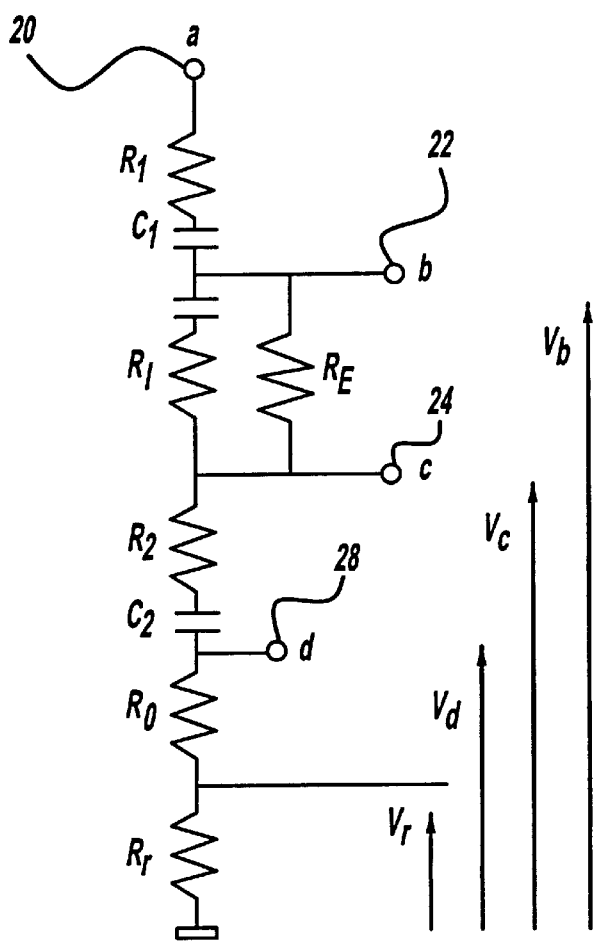
FIG. 6 is a diagram showing a bioelectrical model of the human body.

FIG. 6 shows this measurement principle, and indicates the various connection points of the electrodes 20, 22, 24 and 26. As shown in this figure, a voltage $V_d$ is measured at the terminal 26, a voltage $V_c$ is measured at the terminal 24 and a voltage $V_b$ is measured at the terminal 22. The measured values and the weight of the person are then transmitted to the calculator unit 14 which determines in real time the fat body mass, the lean body mass and the amount of water contained in the body of the person.

In a second embodiment of the invention the current signal 11 is canceled in the middle of each half-wave, as shown in FIG. 8, which totally cancels the voltage $V_c$. This improves the stability of the measured voltage 30.

The first module 6 can be integrated into conventional scales for weighing persons. It can equally be used to monitor the progress of a treatment intended to assess the nutritional requirements of a person. The device in accordance with the invention can also be used to indicate changes in the local body composition of a person during a cellulite treatment session or a massage session.

There is claimed:

1. A method for measuring a bioelectrical impedance of a person's body, said method comprising the steps of:

applying at least a first and a second pair of electrodes on a person's body;

applying a periodic electrical signal having a square wave shape between said first pair of electrodes connected to said body;

measuring voltage values between said at least second pair of electrodes also connected to said body, at times when a capacitive component of said voltage value is cancelled due to the square shape of said electrical signal;

determining from said measured voltage values a bioelectrical impedance value; and displaying said bioelectrical impedance value.

2. The method claimed in claim 1 further comprising the steps of:

measuring a weight value of said person; and determining and displaying a fat body mass, a lean body mass and an amount of water contained in said person's body from said weight value and said bioelectrical impedance value.

3. The method claimed in claim 1 further comprising a step of adjusting a period of said electrical signal by said processor unit as a function of measurements to be performed.

4. The method claimed in claim 1 further comprising a step of cancelling said electrical signal in a middle of each half-wave so as to totally cancel the capacitive effect of said body.

5. A device for measuring the composition of the body of a person, said device comprising:

a first electronic module adapted to measure a bioelectrical impedance and including at least one current source adapted to deliver a periodic electrical having a square wave shape, said current source being connected to two excitation electrodes adapted to be connected to a person's body; and a measuring unit for measuring a voltage value between two measuring electrodes adapted to be connected to said body;

a computing module comprising means for determining a bioelectrical impedance of said body as a function of voltage values provided by said measuring unit; and a display unit for displaying said bioelectrical impedance.

6. The device claimed in claim 5 wherein said computing module further comprises means for determining an intracellular impedance and an extracellular impedance of said person's body from said voltage value.

7. The device claimed in claim 5 further comprising a second electronic module for measuring a weight of said person's body, said computing module further comprising means for determining from the measured weight and said measured bioelectrical impedance of a fat body mass, a lean body mass and an amount of water contained in said body.

8. The device claimed in claim 5 wherein said electrical signal has a frequency chosen in the range of 2–400 kHz.

9. Scales for weighing a person comprising:

an upper horizontal pan;

a first electronic module for measuring a weight of a person standing on said pan;

a second electronic module for measuring a bioelectrical impedance of said person, said second electronic module including at least one current source adapted to deliver a periodic electrical signal of square wave shape which is applied to the body of said person through a first pair of electrodes and a measuring unit for measuring a voltage value between a second pair of electrodes, said first and second pair of electrodes being disposed to be in contact with said body when said person is standing on said pan;

a computing module for determining a bioelectrical impedance of said body as a function of said voltage value and a fat body mass, a lean body mass and an amount o water contained in said body as function of said bioelectrical impedance and said measured weight; and display means for displaying said bioelectrical impedance, said fat body mass, said lean body mass and said amount of water contained in said body.

* * * * *